United States Patent [19]

Eibofner

[11] 4,071,954
[45] Feb. 7, 1978

[54] TURBINE INSERT FOR THE HEAD OF A DENTAL TURBINE ELBOW

[75] Inventor: Eugen Eibofner, Biberach an der Riss, Germany

[73] Assignee: Kaltenbach & Voigt, Biberach an der Riss, Germany

[21] Appl. No.: 713,280

[22] Filed: Aug. 10, 1976

[30] Foreign Application Priority Data

Aug. 28, 1976 Germany ............................. 2618739

[51] Int. Cl.² .............................................. A61C 1/10
[52] U.S. Cl. ........................................ 32/27; 415/503
[58] Field of Search ...................... 415/503, 112; 32/27

[56] References Cited

U.S. PATENT DOCUMENTS

| | | | |
|---|---|---|---|
| 2,945,299 | 7/1960 | Fritz | 32/27 |
| 3,077,333 | 2/1963 | Gotwald, Jr. et al. | 415/503 |
| 3,123,338 | 3/1964 | Borden | 415/503 |
| 3,210,848 | 10/1965 | Bizzigotti | 415/503 |
| 3,268,205 | 8/1966 | Allen et al. | 415/503 |
| 3,324,553 | 6/1967 | Borden | 415/503 |
| 3,411,210 | 11/1968 | Staunt | 415/503 |
| 3,469,318 | 9/1969 | Saffir | 415/503 |
| 3,471,125 | 10/1969 | Taubald et al. | 415/503 |
| 3,952,416 | 4/1976 | Lingenhole | 32/27 |
| 3,962,789 | 6/1976 | Flatland | 32/27 |

FOREIGN PATENT DOCUMENTS 2,214,031   10/1972   Germany ............................. 415/503

*Primary Examiner*—C. J. Husar
*Attorney, Agent, or Firm*—Haseltine, Lake & Waters

[57] ABSTRACT

A turbine insert for insertion into a head-housing of a turbine elbow for dental use includes a rotatable axle which has a plurality of turbine blades disposed thereon. One of the axle-ends is adapted to receive a dental tool and a threaded cap may be attached to the head-housing. Support means are provided for receiving the rotatable axis, and the other axle-end is rotatably supported in the threaded cap through the support means. A protective sleeve which surrounds the turbine blades is formed with an opening for the passage of compressed air for driving the turbine, and at least partially surrounds and rotatably supports the dental-tool receiving axle-end through the support means.

11 Claims, 5 Drawing Figures

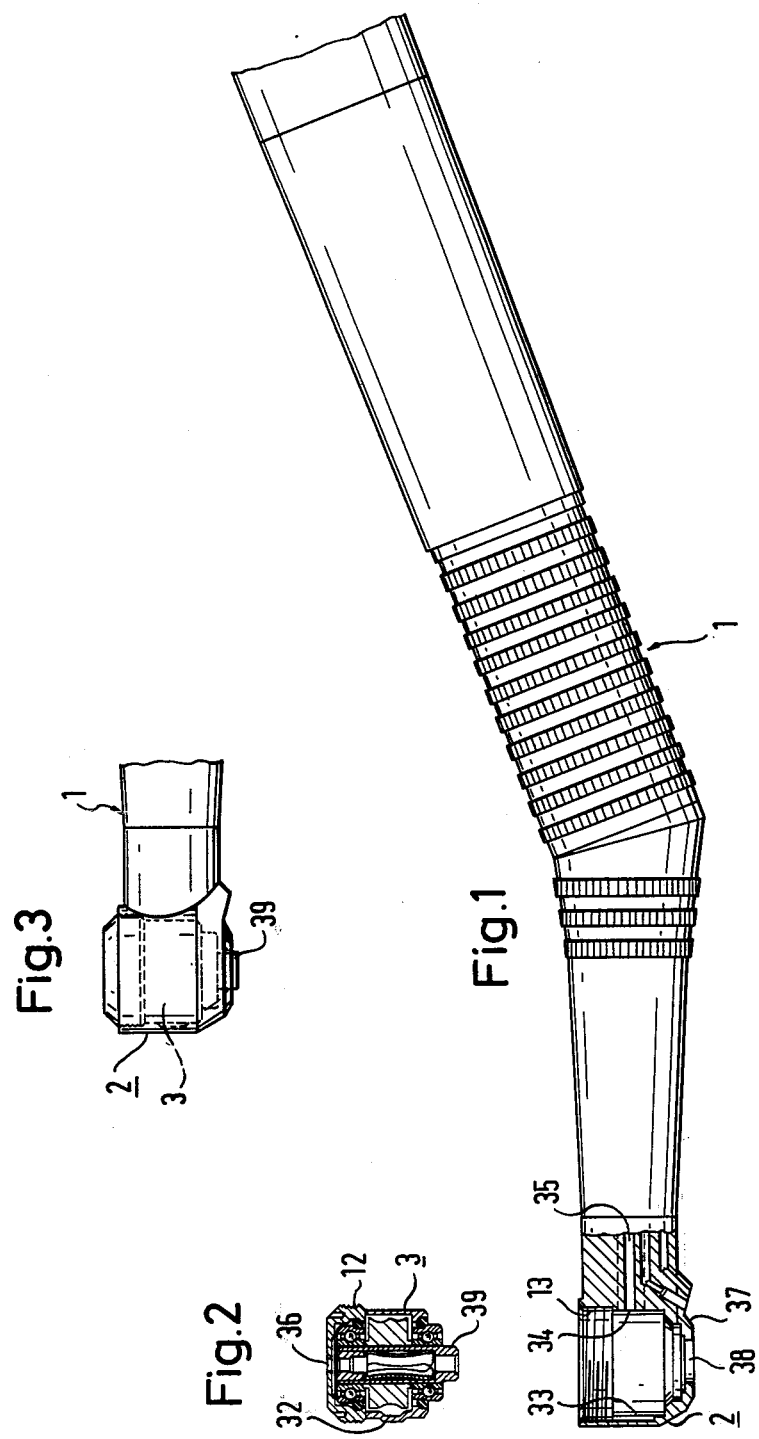

TURBINE INSERT FOR THE HEAD OF A DENTAL TURBINE ELBOW

BACKGROUND OF THE INVENTION

1. Field of the Invention

The invention relates to a turbine insert insertable into the head of a dental turbine-elbow and includes a rotatable shaft provided with turbine blades, one end thereof being formed for receiving a dental tool, for example, a drill, the other end thereof being rotatably supported in a cap which may be screwed on the head housing by means of a bearing.

In the event of any damage to a turbine-insert of this type or a component thereof, the whole turbine-insert may be easily and quickly removed by unscrewing the cap from the head housing, and by replacing it with a new and undamaged turbine insert, which facilitates the repair of such a damage by the dentist or his assistant.

2. Description of the Prior Art

A well known turbine insert of this type is known in the prior art, in which the turbine blades as well as the side of the shaft carrying the tool and a bearing associated with the shaft are accessible when not inserted into the head housing, so that a special protective cap is required, for example, for transportation, in order to protect the accessible and sensitive parts from damage prior to the assembly being inserted into the head housing. Insertion into the head housing is furthermore difficult, since the accessible parts project laterally with respect to the shaft, and therefore may impinge on the walls of the head housing upon insertion thereinto and be damaged thereby. Damage of this kind renders the whole turbine insert useless. Furthermore impingement of the support associated with the tool portion of the shaft with the walls of the head housing may result in a displacement of that support and a change of its alignment with respect to the rotatable shaft, resulting in a misalignment, so that the rotatability and life span of the turbine-insert are impaired.

Although a turbine insert is known from Austrian Pat. No. 235,466 having a support disposed on the shaft facing away from the tool portion, and where the turbine blades are surrounded by respective ring-shaped housings, the support associated with the tool side, or facing the tool side, is also accessible in this known device, so that the latter is saddled with the same disadvantages. As a result of the use of the above-named ring-shaped housing, the turbine insert is open on the end thereof facing away from the tool portion, making it necessary for a special cover to be screwed onto the head of the housing upon insertion of the turbine-insert thereinto, so that the turbine-insert is clamped in an axial direction. This may lead to misalignment of the components of the turbine-insert. Furthermore the special cover results in a relatively large height of the closed head-housing, which causes difficulties in the mouth of a patient during treatment. The special cover may furthermore be lost.

Furthermore, there is known a turbine-insert from German prosecuted Pat. No. 1,061,063, in which the rotatable shaft and the adjacent supports are disposed in a cap which may be screwed onto the head housing, the cap being formed with an opening permitting the passage of the dental tool. The turbine blades disposed in this case on the portion of the rotatable shaft facing away from the tool may, however, be damaged during transport, or insertion of the turbine-insert into the head housing.

OBJECTS OF THE INVENTION

It is an object of the present invention to devise a turbine-insert of the aforementioned kind, where damage to component parts not covered or protected by a cap, or misalignment thereof are to be avoided upon insertion of these components into the housing, and where damage to these components is avoided also during transport or the like without the necessity of a protective cap, which must, in any case, be removed prior to use.

SUMMARY OF THE INVENTION

The objects of the invention are attained by the turbine blades and the end portion of the rotatable axle facing away from the tool being at least partly surrounded by a protective sleeve, in which the end portion of the rotatable axle facing the tool is supported by means of a bearing, and which is formed with an opening for passage of compressed air for driving the turbine. By the provision of the protective sleeve serving simultaneously for support of the section of the rotatable axle carrying the tool, the turbine blades and the supports facing the tool-carrying side of the rotatable axles are afforded permanent protection. Since the above-cited support is held rigid with respect to the rotatable axle by the protective sleeve, the support is not displaceable, so that the alignment thereof with respect to the rotatable axle is not impaired and misalignments are avoided. The turbine insert may now be completely tested during manufacture, and the components ultimately aligned with one another.

The threaded cap and the protective sleeve are component parts separated from one another, and mutually rotatable with respect to one another, which is of particular advantage upon screwing the threaded cap onto the head-housing particularly when the protecting sleeve includes an outwardly projecting guide lip or guide portion for engaging a corresponding recess formed on the inner side of the wall of the head-housing for forcible alignment of the opening formed in the protecting sleeve with an orifice of a compressed air supply for the elbow. It is then possible to insert the protective sleeve with its guiding lip into the guiding recess formed in the head-housing, and then to screw the protective cap onto the head-housing in rotating it with respect to the protective sleeve. Avoidance of a special protective cover, as used, for example, in the aforecited Austrian patent, permits a relatively low height of the head-housing, which in turn makes it possible for the turbine-insert to be small, so that a miniature turbine may be used. Neither can the turbine blades be damaged during transport or insertion into the head-housing.

In a further development of the proposed turbine insert the ring-shaped front end of the threaded cap and the ring-formed front end of the protective sleeve are disposed next to one another. This results in a mutual stabilization of the threaded cap and the protecting sleeve.

Cohesion of the component parts of the turbine-insert is favorably influenced by elastic abutment elements being provided between the two supports of the rotatable axle and the walls of the straight cap surrounding the rotatable axle, as well as the protective sleeve, which permits a detachable clamping of the threaded cap and the protective sleeve to the rotatable axle. The abutment element may be implemented in the form of O-rings made of elastic material.

It is further advantageous if the threaded cap and the protective sleeve are formed with respective inwardly projecting and ring-shaped projections at some distance from their ring-formed front sides facing the tool side, the 0-rings abutting these projections axially in a direction towards the turbine blades. The mutual stabilization of the threaded cap and the protective sleeve is further improved, if the threaded cap is formed with a second projection spaced somewhat from its inwardly projecting ring-shaped projection, the O-ring axially abutting the second projection in the direction away from the turbine blades, whereby the second projection of the side cap may be formed by its floor. It is further advantageous, if the two supports of the rotatable axle are formed with respectively outwardly facing projections, spaced at some distance from their respective ends facing the turbine blades, the O-rings axially abutting these outwardly facing projections in a direction away from the turbine blades, respectively. An easy mutual abutment of the two aforesaid ring-shaped front ends of the threaded cap and the protective sleeve is made possible under pressure by the proposed projections of the O-rings, which permits an optimal mutual stabilization of the threaded cap and the protecting sleeve.

The supports of the rotatable shaft may be formed by sliding supports, air supports or the like. It is advantageous if both supports of the rotatable shaft are formed by ball bearing supports, the outwardly projecting support being disposed on the outer rim of the ball bearing.

BRIEF DESCRIPTION OF THE DRAWING

The invention will be better understood by means of the accompanying drawing which shows various versions of the invention.

FIG. 1 shows a partially cross-sectional side view of the turbine containing portion of a dental turbine-elbow with an associated head-housing;

FIG. 2 shows the turbine-insert insertable into the head-housing in cross-section;

FIG. 3 shows the head-housing with the inserted turbine-insert;

DESCRIPTION OF THE PREFERRED EMBODIMENTS

Figure 4:
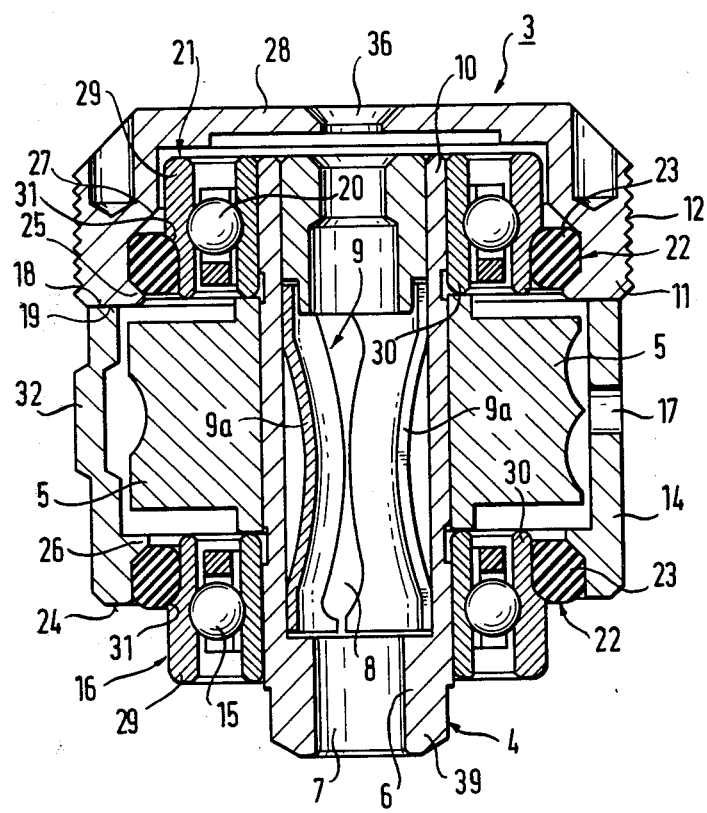
FIG. 4 shows the enlarged turbine-insert according to FIG. 2.

The turbine-elbow for dental use shown in FIG. 1 is provided on the left-side thereof, as shown in the drawing, with a head-housing 2, a turbine-insert 3 being insertable in the latter.

The turbine-insert 3 includes, as seen in FIG. 4, a rotatable axle 4, which includes in an inner third thereof a plurality of turbine blades 5. The lower end portion 6 of the rotatable axle 4 shown in FIG. 4 is formed with an opening 7 for receiving a non-illustrated shaft of a dental tool, for example a drill, the opening 7 forming the orifice of a recess 8 for receiving the aforesaid shaft of the rotatable axle 4. A collet 9 having clasps 9a for clamping the aforesaid shaft is disposed in the recess 8. The axle 4 is rotatably supported in a threaded cap 11 by means of a support 21, which is implemented as a ball bearing 20, the threaded cap 11 being screwable onto the head-housing 2. The cap 11 is formed with an outer thread 12, and the head-housing 2 with an inner thread 13 for the former to be screwed onto the latter, as can be also seen from FIGS. 1 and 2.

The turbine blades 5 and a portion of the lower, or tool carrying end portion 6 of the rotatable axle 4 adjoining thereto are surrounded by a protective sleeve 14, the tool-carrying end-portion 6 of the axle 4 being supported therein by means of a support generally designated as 16 and implemented specifically as a ball bearing 15. The protective sleeve 14 is formed with an opening 17 for permitting compressed air for driving the turbine to enter therethrough.

The ring-shaped front end 18 of the threaded cap 11, and the ring-shaped front end 19 of the protecting cover 14 facing the latter abut each other.

Elastic abutment elements 22 are provided between the support 16 and the wall of the protective cap 11 surrounding the rotatable axle 4, and between the support 21 and the protective covering 14, respectively, the abutment elements 22 including respective O-rings 23 made of synthetic material, such as rubber.

Figure 5:
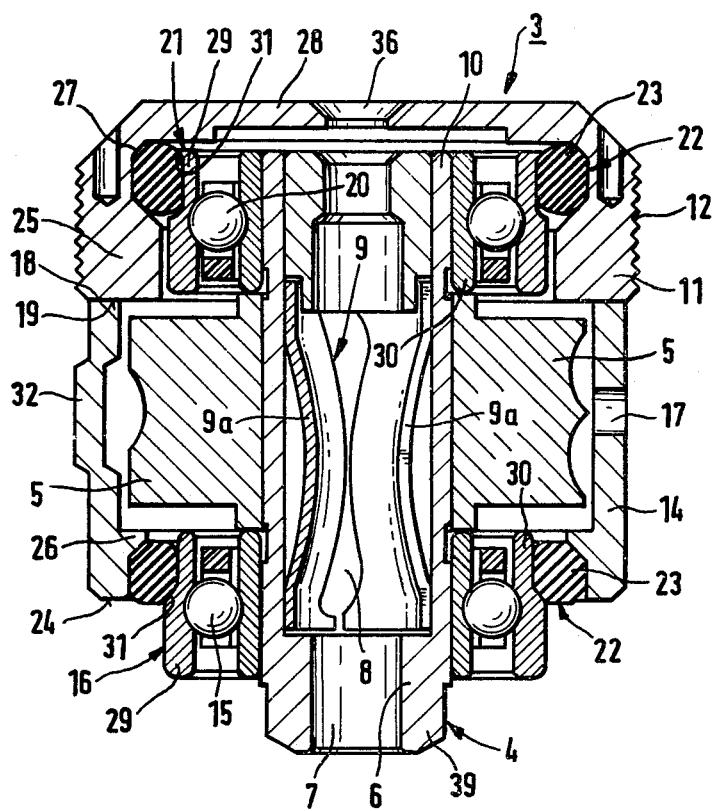
FIG. 5 is an alternate version of FIG. 4.

It will be further seen from FIG. 4 that the ring-shaped front end 18 of the threaded cap 11, and the ring-shaped front end 24 of the protecting cover 14 are provided with respective ring-shaped projections 25 and 26 facing inwardly, the projection 26 being formed at some distance from the tool-facing front end 24, respective O-rings 23 abutting axially against respective projections 25 and 26 in a direction towards the turbine blades 5. The threaded cap 11 is further formed with a second inwardly facing and ring-shaped projection 27 spaced at some distance from the inwardly facing ring-shaped projection 25, one of the O-rings 23 abutting against the projection 27 axially in a direction away from the turbine blades 5. The second projection 27 of the threaded cap 11 may also be formed, as shown in FIG. 5, by the floor 28 of the cap 11. The outer rings 29 of the respective ball bearings 15 and 20 are formed with respectively outwardly facing projections 31 at some distance from the ends thereof facing the turbine blades 5, respective O-rings 23 abutting the projections 31 axially in a direction facing away from the turbine blades 5.

The protective sleeve 14 is formed with an outwardly projecting lip or member 32 for engaging a corresponding recess 33 shown best in FIG. 1, which is formed on the inner side of the wall of the head-housing 2 for forcible alignment of the orifice 34 of a compressed air supply 35 of the elbow 1 with the opening 17 of the protective cover 14.

A further non-illustrated opening can be formed in the protective cover 14 for discharging the turbine exhaust air, which may be spaced, for example, at an angular distance of 120° with respect to the opening 17. The turbine exhaust air may also be discharged through the ball bearings 15 and 20 and through an opening 36 formed in the floor 28 of the threaded cap 11, the opening 36 being formed for the introduction of a pin for expelling or discharging the tool.

As can best be seen from FIG. 1, the floor 37 of the head-housing 2 is formed with an opening 38 for permitting passage of the tool carrying end 39 of the lower end portion 6 of the rotatable axle 4.

While there has been shown what is considered to be the preferred embodiment of the invention, it will be obvious that modifications may be made which come within the scope of the disclosure of the specification.

What is claimed is:

1. A turbine insert for insertion into a head-housing of a turbine elbow for dental use comprising: a rotatable axle having two ends and a plurality turbine blades disposed thereon, one of the axle-ends being adapted to receive a dental tool; a threaded cap attachable to the head-housing; support means for receiving said rotatable axle, the other of the axle-ends being rotatably supported in said threaded cap through said support means; and a protective sleeve surrounding said turbine blades, formed with an opening for the passage of compressed air for driving the turbine, and at least partially surrounding and rotatably supporting the dental-tool receiving axle-end through said support means, said threaded cap, said rotatable axle and said support means for said axle being combined into a single unit before insertion into said head housing.

2. A turbine-insert according to claim 1 wherein said threaded cap and said protective sleeve are formed with ring-shaped front ends facing and abutting each other, respectively.

3. A turbine insert according to claim 2 wherein said support means includes first and second supports and said threaded cap is formed with a wall surrounding said axle, and further comprising first and second elastic abutment elements disposed between said first support and said wall, and between said second support and said protective sleeve, respectively.

4. A turbine insert according to claim 3 wherein each of said abutment elements includes an O-shaped ring of elastic material.

5. A turbine-insert according to claim 4 wherein the ring-shaped front ends of said threaded cap and said protective sleeve are formed with inwardly facing ring-shaped projections, respectively, the inwardly facing ring-shaped projection of said protective sleeve being spaced from the ring shaped front end thereof, said O-shaped rings respectively abutting said inwardly facing ring-shaped projections axially in a direction facing said turbine blades.

6. A turbine insert according to claim 5 wherein said threaded cap is formed with a second inwardly facing ring-shaped projection spaced from the first inwardly facing ring-shaped projection, one of said O-shaped rings abutting against said second projection in a direction facing away from said turbine blades.

7. A turbine insert according to claim 6 wherein said threaded cap includes a floor forming said second projection.

8. A turbine insert according to claim 5 wherein each of said supports has an end facing said turbine blades and is formed with an outwardly facing projection spaced from the turbine-blade facing-end thereof, said O-shaped rings axially abutting said outwardly facing projections, respectively, in a direction facing away from said turbine blades.

9. A turbine insert according to claim 8 wherein said first and second supports include first and second ball-bearing supports having first and second outer rings, respectively, each of said outwardly facing projections being disposed on one of said outer rings, respectively.

10. A turbine insert according to claim 1 further comprising the turbine elbow and the head-housing, and wherein the latter includes a wall formed with a guidance recess, and the former includes a compressed air supply formed with an orifice, said protective sleeve being formed with an outwardly projecting guidance lip for engaging said guidance recess for forcible alignment of the protective-sleeve openings with the orifice of said compressed air supply.

11. A turbine insert for insertion into a head-housing of a turbine elbow for dental use comprising: a rotatable axle having two ends and a plurality turbine blades disposed thereon, one of the axle-ends being adapted to receive a dental tool; a threaded cap attachable to the head-housing; support means for receiving said rotatable axle, the other of the axle-ends being rotatably supported in said threaded cap through said support means; and a protective sleeve surrounding said turbine blades, formed with an opening for the passage of compressed air for driving the turbine, and at least partially surrounding and rotatably supporting the dental-tool receiving axle-end through said support means, said threaded cap, said rotatable axle and said support means for said axle being combined into a single unit before insertion into said head housing; said threaded cap and said protective slecve being formed with ring-shaped front ends facing and abutting each other, respectively; said support means including first and second supports and said threaded cap being formed with a wall surrounding said axle, and further comprising first and second elastic abutment elements disposed between said first support and said wall, and between said second support and said protective sleeve, respectively; each of said abutment elements including an O-shaped ring of elastic material; the ring-shaped front ends of said threaded cap and said protective sleeve being formed with inwardly facing ring-shaped projections, respectively, the inwardly facing ring-shaped projection of said protective sleeve being spaced from the ring-shaped front end thereof, said O-shaped rings respectively abutting said inwardly facing ring-shaped projections axially in a direction facing said turbine blades; said threaded cap being formed with a second inwardly facing ring-shaped projection spaced from the inwardly facing ring-shaped projection, one of said O-shaped rings abutting against said projection in a direction facing away from said turbine blades; said threaded cap including a floor forming said second projection; each of said supports having an end facing said turbine blades and being formed with an outwardly facing projection spaced from the turbine-blade facing-end thereof, said O-shaped rings axially abutting said outwardly facing projections, respectively, in a direction facing away from said turbine blades; said first and second supports including first and second ball bearing supports having first and second outer rings, respectively, each of said outwardly facing projections being disposed on one of said outer rings, respectively; said head-housing including a wall formed with a guidance recess, said turbine elbow including a compressed air supply formed with an orifice, said protective sleeve being formed with an outwardly projecting guidance lip for engaging said guidance recess for forcibly alignment of the protective-sleeve openings with the orifice of said compressed air supply.

* * * * *